US008372826B2

(12) United States Patent
Voskuhl

(10) Patent No.: US 8,372,826 B2
(45) Date of Patent: *Feb. 12, 2013

(54) ESTRIOL THERAPY FOR MULTIPLE SCLEROSIS AND OTHER AUTOIMMUNE DISEASES

(75) Inventor: Rhonda R. Voskuhl, West Hollywood, CA (US)

(73) Assignee: The Regents of the University of California, Oakland, CA (US)

( * ) Notice: Subject to any disclaimer, the term of this patent is extended or adjusted under 35 U.S.C. 154(b) by 1672 days.

This patent is subject to a terminal disclaimer.

(21) Appl. No.: 11/151,040

(22) Filed: Jun. 13, 2005

(65) Prior Publication Data
US 2005/0239762 A1    Oct. 27, 2005

Related U.S. Application Data

(63) Continuation of application No. 10/131,834, filed on Apr. 24, 2002, now Pat. No. 6,936,599.

(60) Provisional application No. 60/286,842, filed on Apr. 25, 2001.

(51) Int. Cl.
*A61K 31/56* (2006.01)
*A01N 45/00* (2006.01)

(52) U.S. Cl. .......................... 514/182; 514/171

(58) Field of Classification Search ................... 514/171
See application file for complete search history.

(56) References Cited

U.S. PATENT DOCUMENTS

| | | | | |
|---|---|---|---|---|
| 5,200,197 | A | * | 4/1993 | Wright et al. ................. 424/473 |
| 6,013,642 | A | | 1/2000 | Foulkes et al. |
| 6,043,236 | A | * | 3/2000 | Brattsand et al. ............ 514/182 |
| 6,214,791 | B1 | * | 4/2001 | Arnon et al. ...................... 514/2 |

FOREIGN PATENT DOCUMENTS

| | | |
|---|---|---|
| WO | WO 97/08188 | 3/1997 |
| WO | 99/48502 | 9/1999 |
| WO | WO 01/85154 | 11/2001 |
| WO | 03/072109 | 9/2003 |
| WO | 03/072110 | 9/2003 |

OTHER PUBLICATIONS

Kim, S.; Liva, S.M.; Dalai, M.A.; Verity, M.A.; Voskuhl, R..IC Estriol ameliorates autoimmune demyelinating disease: Implications for multiple sclerosis. Neurology. Apr. 12, 1999.52(6): 1230-1238.*
Abramsky, O., *Pregnancy and multiple sclerosis*, Annals of Neurology 1994, 36 Suppl: S38-41.
Abaroni R. et al., *Bystander suppression of experimental autoimmune encephalomyelitis by T cell lines and clones of the Th2 type induced by copolymer 1*, Journal of Neuroimmunology 1998, 91:135-46.
Ando, E. et al., *Encephalitogenic T Cells in the B10PL Model of Experimental Allergic Encephalomyelitis (EAE) Are of the Th1 Lymphokine Subtype*, Cell. Immunol., 124:132-143, 1989.
Asthana, S. et al., *High-Dose Estradiol Improves Cognition for Women with AD: Results of a Randomized Study*, Neurology 2001, 57:605-12.
Balashov et al., *Defective Regulation of IFNgamma and IL-12 by endogenous IL-10 in progressive MS*, Neurology 2000, 55:192-8.
Barkhof, F. et al., *T(1) hypointense lesions in secondary progressive multiple sclerosis: effect of interferon beta-1b treatment*, Brian 2001, 124:1396-402.
Barkley, M.S. et al., *Equol: a contributor to enigmatic immunoassay measurements of estrogen*, Steroids 1985, 46:587.
Bebo, B.F. Jr. et al., *Low-dose estrogen therapy ameliorates experimental autoimmune encephalomyelitis in two different inbred mouse strains*, Journal of Immunology, Feb. 1, 2001, 166(3):2080-9.
Becker, C.C. et al., *Immunotherapy in Multiple Sclerosis*, Amer. Journal of Health System Pharmacy, Oct. 1, 1995, 52(19):2105-20.
Bijisma, J.W. et al., *Estrogens and Rheumatoid Arthritis*, American Journal of Reproductive Immunology, 1992, 28:231-234.
Birk, K. et al., *The Clinical Course of Multiple Sclerosis During Pregnancy and the Puerperium*, Arch Neurol 1990, 47:738-42.
Birk, K. et al., *Pregnancy and Multiple Sclerosis*, Semin Neurol 1998, 8:205-13.
Bongioanni et al., *Systemic High-Dose Recombinant-alpha-2a-Interferon Therapy Modulates Lymphokine Production in Multiple Sclerosis*, J. Nuerolog. Sci., Nov. 1996, 143(1-2):91-99.
Boothman, B.R., *Interferon Beta: The Current Position*, British Jour. of Hospital Medicine, Mar. 19-Apr. 1, 1997, 57(6):277-80.
Boumpas, D.T. et al., *Systemic Lupus Erythematosus: Emerging Concepts*, Annals of Internal Medicine 1995, 123:42-53.
Brod, S.A. et al., *Multiple Sclerosis: Clinical Presentation, Diagnosis and Treatment*, Amer. Family Physician, Sep. 15, 1996, 54(4):1301-6, 1309-11.
Brod, S.A. et al., *Interferon-beta 1b Treatment Decreases Tumor Necrosis Factor-beta and Increases Interleukin-6 Production in Multiple Sclerosis*, Neurology, Jun. 1996, 46(6):1633-1638.
Brostoff et al., *Results of a Phase 1 Clinical Trial of a T-Cell Receptor Peptide Vaccine in Patients with Multiple Sclerosis. 1, Analysis of T-Cell Receptor Utilization in CSF Cell Populations*, Journal of Neuroimmunologym, Jun. 1997, 76(1-2): 15-28.
Cannella, B. et al., *IL-10 Fails to Abrogate Experimental Autoimmune Encephalomyelitis*, Journal of Neuroscience Research, 1996, 45:735-746.
Cardozo, L. et al., *Oestriol in the Treatment of Postmenopausal Urgency: A Multicentre Study*, Maturitas, Dec. 1993, 18(1):47-53.
Cheng, G. et al., *Nylestriol Replacement Therapy in Postmenopausal Women*, Chinese Medical Journal 1993, 106:911-916.
Comi, G. et al., *European/Canadian multicenter, double-blind, randomized, placebo-controlled study of the effects of glatiramer acetate on magnetic resonance imaging-measured disease activity and burden in patents with relapsing multiple sclerosis*, European/Canadian Glatiramer Acetate Study Group, Ann Neuro 2001, 49:290-7.

(Continued)

*Primary Examiner* — Shengjun Wang
*Assistant Examiner* — Timothy E Betton
(74) *Attorney, Agent, or Firm* — McDermott Will & Emery LLP

(57) ABSTRACT

The present invention discloses administering steroid hormones to mammals to treat autoimmune related diseases, more particularly, Th1-mediated (cell-mediated) autoimmune diseases including: multiple sclerosis (MS), rheumatoid arthritis (RA), autoimmune thyroiditis and uveitis. Most preferably the invention is used to treat a patient with a therapeutically effective amount of estriol of 8 milligrams once daily via oral administration to treat the symptoms or prevent the onset of multiple sclerosis.

5 Claims, 4 Drawing Sheets

OTHER PUBLICATIONS

Confavreux, C. et al., *Rate of pregnancy-related relapse in multiple sclerosis*, Pregnancy in Multiple Sclerosis Group, New England Journal of Medicine 1998, 339:285-91.

Correale, J. et al., *Steroid hormone regulation of cytokine secretion by proteolipid protein-specific CD4+ T cell clones isolated from multiple sclerosis patients and normal control subjects*, Journal of Immunology 1998, 161:3365-74.

Crisi, G.M. et al., *Staphylcoccal Enterotoxin B and Tumor-Necrosis Factor-alpha-Induced Relapses of Experimental Allergic Encephalomyelitis: Protection by Transforming Growth Factor-Beta and Interleukin-10*, European Journal of Immunology 1995, 25:3035-3040.

Da Silva, J.A. et al., *The Effects of Gender and Sex Hormones on Outcome in Rheumatoid Arthritis*, Baillieres Clinical Rheumatology, 1992, 6:196-219.

Da Silva, J.A. et al., *The Role of Pregnancy in the Course and Aetiology of Rheumatoid Arthritis*, Clinical Rheumatology 1992, 189-194.

Damek, D.M. et al., *Pregnancy and multiple sclerosis*, Mayo Clinic Proceedings 1997, 72:977-89.

DeGroot, L.J. et al., Endocrinology 1994, vol. 3, Part 9, 2171-2223.

Delassus, S. et al., *Differential Cytokine Expression in Maternal Blood and Placenta During Murine Gestation*, J. Immunol. 1994, 152:2411-2420.

Drew, P.D. et al., *Female sex steroids: effects upon microglial cell activation,*, J Neuroimmunol 2000, 111:77-85.

Duda, P.W. et al., *Glatiramer acetate (Copaxone) induces degenerate, Th2-polarized immune responses in patients with multiple sclerosis*, Journal of Clinical Investigation 2000, 105:967-76.

Follingstad, A.H. et al., *Estriol, the Forgotten Estrogen?*, JAMA 1978, 239:29-30.

Fritzmeier, K.H. et al., *Analysis of the Effects of Erbeta on Eralpha Transcriptional Activity Using Isotope Selective Ligands*, Experimental and Clinical Endocrinology & Diabetes 2001, 109,857.

Gilmore, W. et al., *Effect of estradiol on cytokine secretion by proteolipid protein-specific T cell clones isolated from multiple sclerosis patients and normal control subjects*, Journal of Immunology 1997, 158:446-51.

Hall et al., *A randomized controlled trial of the effect of hormone replacement therapy on disease activity in postmenopausal rheumatoid arthritis*, Annals of the Rheumatic Diseases, Feb. 1994, 53(2):112-6.

Harms, C. et al., *Differential mechanisms of neuroprotection by 17 beta-estradiol in apoptotic versus necrotic neurodegeneration*, J Neurosci 2001, 21:2600-9.

Heman, M.A. et al., *Oral Contraceptives and the incidence of multiple sclerosis*, Neurology, Sep. 26, 2000, 55(6):848-54.

Hill, J.A. et al., *T-Helper I-Type Immunity to Trophoblast in Women with Recurrent Spontaneous Abortion*, JAMA 1995, 273:1933-1936.

Hofbauer, R. et al., *Oral Contraceptives that Contain Ethinyl Estradiol (0.035 mg) and Cyproterone Acetate (2 mg) inhibit Leukocyte Transmigration through Endothelial Cell Monolayers*, Fertility & Sterility, vol. 72, No. 4, Oct. 1999, 652-656.

Hunter, S.F. et al., *Rational Clinical Immunotherapy for Multiple Sclerosis*, Mayo Clinic Proceedings, Aug. 1997, 72(8):765-80.

Ito, A. et al., *Estrogen treatment down-regulates TNF-alpha production and reduces the severity of experimental autoimmune encephalomyelitis in cytokine knockout mice*, Journal of Immunology, Jul. 1, 2001, 167(1):542-52.

Jacobs, L.D. et al., *Intramuscular interferon beta-1a therapy initiated during a first demyelinating event in multiple sclerosis*, Champs Study Group, N Engl J Med 2000, 343:898-904.

Janeway, C.A. et al., *Signal and Signs for Lympocyte Responses*, Cell 1994, 576:275-285.

Jansson, L. et al., *Oestrogen induced suppression of collagen arthritis. IV: Progesterone alone does not affect the course of arthritis but enhances the oestrogen-mediated therapeutic effect*, Journal of Reproductive Immunology 1989, 15:141-50.

Jansson, L. et al., *Estrogen induces suppression of collagen arthritis, V: Physiological level of estrogen in DBA/1 mice is therapeutic on established arthritis, suppresses anti-type II collagen T-cell dependent immunity and stimulates polyclonal B-cell activity*, Journal of Autoimmunity 1990, 3:257.

Jansson, L. et al., *Estrogen induces a potent suppression of experimental autoimmune encephalomyelitis and collagen-induced arthritis in mice*, Journal of Neuroimmunology 1994, 53(2):203-207.

Jenson, J. et al., *Increased T Cell Expression of CD154 (CD40-Ligand) in Multiple Sclerosis*, European Journal of Neurology 2001, 8:321-8.

Jungers, P. et al., *Influence of Oral Contraceptive Therapy on the Activity of Symtemic Lupus Erythematosus*, Arthritis and Rheumatism 1982, 25:618-623.

Kassi, E.N. et al., *Molecular analysis of estrogen receptor alpha and beta in lupus patients*, Eur J Clin Invest 2001, 31:86-93.

Katzenellenbogen,B., *Biology and Receptor Interactions of Estriol and Estriol Derivatives In vitro and In vivo*, The Journal of Steroid Biocehmistry 1984, 20:1033-1037.

Kennedy, M.K. et al., *Analysis of Cytokine mRNA Expression in the Central Nervous System of Mice with Experimental autoimmune Encephalomyelitis Reveals that 1L-10 mRNA Expression Correlates with Recovery*, J. Immunol. 1992, 149:2496-2505.

Kent, Fukaura et al., *Oral Administration of Myelin Induces Antigen-Specific TGF-beta 1-Secreting T Cells in Multiple Sclerosis Patients*, Annals of the New York Academy of Sciences, Apr. 5, 1997, 815:412-422.

Kim, S. et al., *Estriol ameliorates autoimmune demyelinating diseases: Implications for multiple sclerosis*, Neurology, Apr. 12, 1999, 52(6):1230-1238.

Kim, S. et al., *Mechanisms in the Shift toward TH2 during pregnancy: A role for estriol treatment of TH 1 mediated disease*, Annual Meeting of the Professional Research Scientists on Experimental Biology '98, Part 1, San Francisco, California, USA, Apr. 18-22, 1998, FASEB Journal, Mar. 17, 1998, 12(4):A616.

Kirkengen, A.L. et al., *Oestriol in the Prophylactic Treatment of Recurrent Urinary Tract Infection in Postmenopausal Women*, Scan J. Prim. Health Care, 1992, 10:139-142.

Koloszar, S. et al., *Treatment of Climacteric Urogenital Disorders with an Estriol-Containing Ointment*, Orvosi Hetilap, Feb. 12, 1995, 136(7):343-5.

Kozovoska, M.E. et al., *Interferon beta induces T-helper 2 immune deviation in MS*, Neurology 1999, 53: 1692-7.

Krishnan, L. et al., *Pregnancy impairs resistance of C57BL/6 Mice to Leishmania Major Infection and Causes Decreased Antigen-Specific IFN-Responses and Increased production of T Helper 2 Cytokines*, J. Immunol, 1996, 156:644-652.

Krishnan, L. et al., *T-Helper 1 Response Against Leishmania Major in Pregnant C57BL/6 Mice Increases Implantation Failure and Fetal Reabsorptions: Correlation with Increased IFN and TNF and Reduced IL-10 Production by Placental Cells*, J. Immunol 1996, 156:653-662.

Kuchroo, V.K. et al., *Cytokines and Adhesion Molecules Contribute to the Ability of Myelin Proteolipid Protein-Specific T Cell Clones to Mediate Experimental Allergic Encephalomyelitis*, J Immunol 1993, 151:4371-4382.

Lauritzen, C., *Results of a 5 years prospective study of estriol succinate treatment in patients with climacteric complaints*, Hormone and Metabolic Research 1987, 19:579-84.

Lauritzen, C., *The Female Climacteric Syndrome: Significance, Problems, Treatment*, Acta Obstet. Gynecol. Scand. 1976, 51(suppl):49-61.

Lauritzen, C., *The Management of the Premenopausal and Postmenopausal Patient*, Front. Horm. Res. 1973, 2:2-21.

Lemon, H.M., *Estriol Prevention of Mammary Carcinoma Induced by 71,2-dimethylbentanthracene and Procarbazine*, Cancer Research 1975, 35:1341-1353.

Lemon, H.M., *Oestriol and Prevention of Breast Cancer*, Lancet 173, 1:547, 1973.

Li, D.K. et al., *Randomized controlled trial of interferon-beta-1a in secondary progressive MS: MRI results*, Neurology 2001, 56:1505-13.

Lin, H., et al., *SYnthesis of T Helper 2-Type Cyntokines at the Maternal-Fetal Interface*, J. Immunol. 1993, 151:4562-4573.

Liva, S.M. et al., *Testosterone acts directly on CD4+ T-Lymphocytes to increase IL10 production*, Journal of Immunology 2001, 167:2060-2067.

Martin, R. et al., *Immunological Aspects of Demyelinating Diseases*, Annual Review of Immumology 1992, 10:1534-87.

Marzi, M. et al., *Characterization of Type 1 and Type 2 Cytokine Production Profile in Physiologic and Pathologic Pregnancy*, Clin. Exp. Immunol. 1996, 106:127-133.

Matejuk, A. et al., *17beta-estradiol inhibits cytokine, chemokine, and chemokine receptor mRNA expression in the cnetral nervous system of female mice with experimental autoimmune encephalomyelitis*J Neurosci Res 2001, 65:529-42.

Hofbauer, R. et al., *Oral contraceptives that contain ethinyl estrdiol (0.035 mg) and cyproterone acetate (2 mg) inhibit leukocyte transmigration through endathelial cell monolayers*, Fertil Steril 1999, 72:652-6.

Mattsson, R., et al., *Maintained pregnancy levels of oestrogen afford complete protection from post-partum exacerbation of collagen-induced arthritis*, Clinical and Experimental Immunology 1991, 85:41-7

McDonald, W.I. et al., *Recommended Diagnostic Criteria for Multiple Sclerosis: Guidelines from the International Panel on the Diagnostic of Multiple Sclerosis*, Ann Neurol 2001, 50:121-7.

McFarland, H.F. et al., *Using Gadolinium-Enhanced Magnetic Resonance Imaging Lesions to Monitor Disease Activity in Multiple Sclerosis*, Ann. Neurol. 1992, 32:758-766.

Miller, D.H. et al., *Guidelines for the Use of Magnetic Resonance Techniques in Monitoring the Treatment of Multiple Sclerosis*, Annals of Neurology 1996, 39:6-16.

Milner, R., *Understanding the Molecular Basis of Cell Migration: Implications for Clinical Therapy in Multiple Sclerosis*, Clinical Science, Feb. 1997, 92(2):113-22.

Minaguchi, H. et al., *Effect of Estriol on Bone Loss in Postmenopausal Japanese Women: A Multicenter Prospective Open Study*, Journal of Obstetrics and Gynaecology Research, Jun. 1996, 22(3):259-65.

Mosselman, S. et al., *ER beta identification and characterization of a novel human estrogen receptor*, FEBS lett 1996. 392:49-53.

Murray, J.S. et al., *Major Histocompatibility Complex Regulation of T helper Functions Mapped to a Peptide C Terminus that Controls Ligand Density*, Eur. J. Immunol. 1994, 24:2337-2344.

Nelson, J.L. et al., *Remission of Rheumatoid Arthritis During Pregnancy and Maternal-Fetal Class II Alloantigen Disparity*, American Journal of Reproductive Immunology 1992, 28:226-7.

Nelson, J.L., et al., *Maternal-Fetal Disparity in HLA Class II Alloantigens and the Pregnancy-Induced Amelioration of Rheumatoid Arthritis*, N. Eng. J. Med 1993, 329:466-471.

Nishibe, A. et al., *Effect of Estriol and Bone Mineral Density of Lumbar Vertebrae in Elderly and Postmenopausal Women*, Japanese Journal of Geriatrics, May 1996, 33(5):353-9.

Noelle, R.J., *CD40 and its Ligand in Host Defense*, Immunity 1996, 4:415-419.

Offner, H. et al., *Estrogen patentiates treatment with T-Cell receptor protein of female mice with experimental encephalomyelitis*, Journal of Clinical Investigation, May 2000, 105(10):1465-72.

Offner, H. et al., *Estrogen potentiates treatment with TCR protein of female mice with experimental encephalamyelitis* (Joint Annual Meeting of the American Association of Immunologists and the Clinical Immunology Society, Seattle, Washington, USA, May 12-16, 2000), FASEB Journal, Apr. 20, 2000, 14(6):A1246

Offner, H. et al., *Estrogen potentiates treatment with T-cell receptor protein of female mice with experimental encephalomyelitis*, Journal of Clinical Investigation, May 2000, 105(10):1465-1472.

Offner H. et al., *Estrogen potentiates treatment with TCR protein of female mice with experimental encephalomyelitis*(Joint Meeting of the 5$^{th}$ World Congress on Advances in Oncology and the 3$^{rd}$ International Symposium on the Molecular Medicine, Crete, Greece, Oct. 19-21, 2000), International Journal of Molecular Medicine 2000, 6(Supplement 1):S8.

Pary, D.W. et al., *Interferon beta-1b is effective in relapsing-remitting multiple sclerosis, II, MRI analysis results of a multicenter, randomized, double-blind, placebo-controlled trial*, UBC MS/MRI Study Group and the IFNB Multiple Sclerosis Study Group, Neurology 1993, 43:662-7.

Polman, C.H. et al., *The Treatment of Multiple Sclerosis: Current and 25 Future*, Current Opinion in Neurology, Jun. 1995, 8(3):200-9.

Powell, M.D. et al., *Lymphotoxin and Tumor Necrosis factor-Alpha Production by Myelin Basic Protein Specific T Cell Clones Correlates with Encephalitogenicity*, Int. Immunol. 1990, 2:539-544.

Pratt et al., *Estriol Production Rates and Breast Cancer*, Journal of Clinical Endocrinology & Metabolism 1978, 46:44-47.

Rep et al., *Treatment with Depleting CD4 Monoclonal Antibody Results in a preferential Loss of Cicrculating Naive T Cells But Does Not Affect IFN-Gamma Secreting TH1 Cells in Humans*, J. of Clin. Investig., May 1, 1997, 99(9):2225-2231.

Ron, O. et al., *Interleukin-10 Prevents Experimental Allergic Encephalomyelitis in Rats*, Eur. J. Immunol 1994, 24:1434-1440.

Rudick, R.A. et al., *In vivo effects of interferon beta-1a on immunosuppressive cytokines in multiple sclerosis* [published erratum appears in Neurology Jul. 1998, 51(1):332], Neurology 1998, 50:1294-300.

Runmarker, B. et al., *Pregnancy is Associated with a Lower Risk of Onset and a Better Prognosis in Multiple Sclerosis*, Brain 1995, 118:253-61.

Ryan, K.D. et al., *Changes in serum hormone levels associated with male-induced ovulation in group-housed adult female mice*, Endocrinology 1980, 106:959.

Sadovnick, A.D. et al., *Update on Management and Genetics of Multiple Sclerosis*, Jour. of 10 Neural Transmission Supplementum 1997, 50:167-72.

Sanchez-Guerrero, J. et al., *Postmenopausal Estrogen Therapy and the Risk for Developing Systemic Lupus Erythematosus*, Ann. Int. Med. 1995, 122:430-433.

Sandor, S. et al., *Surface-based labeling of corrical anatomy using a deformable atlas*, IEEE Transactions on Medical Imaging 1997, 16:41-54.

Sandyk, R. et al., *Estrogen's impact on cognitive functions in multiple sclerosis*, International Journal of Neuroscience 1996, 86:23-31.

Schiff, I. et al., *Effect of estriol administration on the hypogenadal women*, Fertility and Sterility 1978, 30:278-82.

Schmidt, J.B. et al., *Treatment of Skin Aging with Topical Estrogens*, International Journal of Dermatology, Sep. 1996, 35(9):669-74.

Schmidt, J.B. et al., *New Treatment of Atrophic 20 Acne Scars by Iantophoresis with Estriol and Tretinoin*, International Journal of Dermatology 1995, 34(1):53-7.

Shountz, T. et al., *MHC Genotype Controls the Capacity of Ligand Density to Switch T Helper(Th)-1/Th-2 Priming In Vivo*, J. Immunol. 1996, 157:3893-3901.

Sicotte, N. et al., *Treatment of women with multiple sclerosis using the pregnancy hormone estriol: A Pilot Study* (53$^{rd}$ Annual Meeting of the American Academy of Neurology, Philadelphia, PA, USA, May 5-11, 2001), Neurology Apr. 24, 2001, 56(8 Supplement 3):A75.

Smith, R. et al., *A Pilot Study of the Effect Upon Multiple Sclerosis of the Menopause, Hormone Replacement Therapy and the Menstrual Cycle*, J. Royal See. Med 1992, 85:612-613.

Stinissen, P. et al., *Autoimmune Pathogenesis of Multiple Sclerosis: Role of Autoreactive T Lymphocytes and New Immunotherapeutic Strategies*, Critical Reviews in Immunology 1997, 17(1):33-75.

Suenaga, R. et al., *Peripheral blood T cells and monocytes and B cell lines derived from patients with lupus express estrogen receptor transcripts similar to those of normal cells*, J Rheumatol 1998, 25:1305-12.

Thompson, A.J., *Multiple Sclerosis: Symptomatic Treatment*, J Neurology 1996, 243(8):559-565.

Thorogood, M. et al., *The influence of oral contraceptives on the risk of multiple sclerosis*, British Journal of Obstetrics and Gynaecology, Dec. 1998, 105(12):1296-9.

Trapp, B.D. et al., *Pathogenesis of tissue injury in MS Lesions*, Journal of Neuroimmunology 1999, 98:49-56.

Trapp, B.D. et al., *Axonal pathology in multiple sclerosis: Relationship to neurologic disability*, Current Opinion in Neurology 1999, 12:295-302.

Tringounis, V.A. et al., *Estriol in the Managment of the Menopause*, JAMA 1978, 239:1638-1641.

Utian, W., *The Place of Oestriol Therapy After Menopause*, Acta Endocrinologic Suppl. 1980, 233:51-56.

Vakil, D. et al., *Benign Breast Disease: Estriol Proportions and Family History of Breast Cancer*, Cancer Detection and Prevention 1981, 4:517-523.

Van Boxel-Dezaire, A.H. et al., *Decreased interleukin-10 and increased interleukin-12p40 mRNA are associated with disease activity and characterize different disease stages in multiple sclerosis*, Ann Neurol 1999, 45:695-703.

Krishnan, L. et al., *T helper 1 response against Leishmania major in pregnant C57BL/6 mice increases implantation failure and fetal resarptions. Correlation with increased IFN-gamma and TNF and reduced IL-10 production by placental cells*, Journal of Immunology 1996, 156:653-62.

Vandenbark, A.A. et al., *TCR peptide therapy in human autoimmune diseases*, Neurochem Res 2001, 26:713-30.

Vandenbark et al., *Treatment of Multiple Sclerosis with T-Cell Receptor Peptides: Results of a Double-Blind Pilot Trial*, Nature Medicine, Oct. 1996, 2(10):1109-1115.

Verghese, J. et al., *Cognitive performance in surgically menopausal women on estrogen*, Neurology 2000, 55:872-4.

Villard-Mackintosh, L. et al., *Oral Contraceptives and Reproductive Factors in Multiple Sclerosis Incidence*, Contraception 1993, 47:161-168.

Volpe, A. et al., *Benefits and Risks of Different Hormonal Replacement Therapies in Post-Menopausal Women*, Maturitas 1986, 8:327-334.

Voskuhl, R.R. et al., *Female Sex Hormones at Supraphysicologic but not Physiologic Levels Decrease EAE Sevarity in Female SJL Mice*, FASEB Journal 2001, 15:A372.

Voskuhl, R.R. et al., *Sex hormones and experimental autoimmune encephalomyelitis: Implications for multiple sclerosis*, The Neuroscientist 2001, 7:258-70.

Voskuhl, R.R. et al., *A functional Basis for the association of HLA class II genes and susceptibility to multiple sclerosis; Celluar immune responses to myelin basic protein in a multiplex family*, Journal of Neuroimmunology 1993, 42:199-207.

Watkins-Smith, O. et al., *Quantitative Estimation of Estrogen Conjugates in Late 20 Pregnancy Plasma*, J. Clin. Endocrional 1965, 25:735-741.

Wegmann, T.G. et al., *Bidirectional Cytokine Interactions in the Maternal-Fetal Relationship: Is Successful Pregnancy a Th2 Phenomenon?*, Immunol. Today 1993, 14:353-356.

Zorgdrager, A. et al., *Menstrually Related Worsening of Symptoms in Multiple Sclerosis*, Journal of the Neurologicald Sciences 1997, 149:95-7.

Du, C. et al., *Administration of dehydroeplandrosterone suppresses experimental allergic encephalomyelitis in EJL1J mice*, Journal of Immunology 2001, 7094-7101.

Head, K.A.,*Estriol: Safety and efficacy*, Alternative Med. Rev. 1998, 3:101-113.

Hernan, M.A. et al., *Oral contraceptives and the incidence of multiple sclerosis*, Neurology 2000, 55:848-854.

Jansson, L. et al., *Estrogen-mediated immunosuppression in autoimmune diseases*, Imflammation research 1998, 47:290-301.

Jover, T. et al., *Estrogen protects against global ischemia-induced neuronal death and prevents activation of apeptpic signaling cascades in the hippocampal CA1*, J. Neurosci. 2002, 22:2115-2124.

Lee, S.J. et al., *Neurotrophic and neuroprotective actions of estrogens and their therapeutic implications*, Ann Rev. Pharmacol Toxical 2001, 41:569-591.

Leranth, C. et al., *Estrogen is essential for maintaining nigrostriatal dopamine neurons in primates: Implications for Parkinson's disease and memory*, J. Neurosci 2000, 20:8604-8609.

Maki, P.M. et al., *Enhanced verbal memory in nondemented elderly women receiving hormone-replacement therapy*, Am J. Psychiatry 2001, 158:227-233.

Maki, P.M. et al., *Implicit memory varies across the mentrual cycle: Estrogen effects in young women*, Neuropsychologia 2002, 40:518-529

Murphy, D.D. et al., *Estadiol Increases dendritic spine density by reducing GABA neurotransmission in hippocampal neurons*J. Neurosci 1998, 18:2550-2559.

Rice, M.M. et al., *Postmenopausal estrogen and estrogen-progestin use and 2-year rate of cognitive change in a cohort of older Japanese American women: The Kame Project*, Arch Inter Med. 2000, 160:1641-1649.

Rudick, R.A. et al., *Use of the brain parenchymal fractin to measure whole brain atrophy in relapsing-remitting MS*, Multiple Sclerosis Collaborative Research Group, Neurology 1999, 53:1698-1704.

Sicotte, N.L. et al., *Treatment of multiple sclerosis with the pregnancy hormone estriol*, Ann. Neurology 2002, 52:421-428.

Van Vollenhoven, R.F. et al., *Estrogen, progesterone, and testosterone: Can they be used to treat autoimmune diseases?*, Cleveland Clinic Journal of Medicine 1994, 61:276-284.

Vanderhorst, V.G. et al., *Estrogen induces axonal outgrowth in the nucleus retroambiguus-lumbosacral motoneuronal pathway in the adult female cat*, J. Neurosci, 17:1122-1136.

Voskuhl, R.R. et al., *Hormone-based therapies in MS*, International MS Journal, vol. 10, No. 2, 61-66, 2003.

[No Author], *Risks and benefits of estrogen plus progesting in healthy postmenopausal woemn: Principal results from the Women's Health Initiative randomized controlled trial*, JAMA 2002, 288:321-333.

Behl, C. et al., *17-Beta estradiol protects neurons from oxidative stress-induced cell death in vitro*, Biochem Biophys Res. Commum. 1995, 216:473-482.

Behl, C. et al., *Neuroprotection against oxidative stress by estrogens: Structure-activity relationship*, Mol. Pharmacol. 1997, 51:535-541.

Cutolo, M., *Sex hormone adjuvant therapy in rheumatoid arthritis*, Rheum. Dis. Clin North Am 2000, 26:881-895.

Drake, E.B. et al., *Associations between circulating sex steroid hormones and cognition in normal elderly women*, Neurology 2000, 54:599-603.

Drossaers-Bakker, K.W. et al., *Pregnancy and oral contraceptive use do not significantly influence outcome in long term rheumatoid arthritis*, Ann. Rheum. Dis. 2002, 61:405-408.

International Search Report issued by the International Searching Authority for PCT/US2002/013,407 mailed Aug. 22, 2002.

* cited by examiner

| Pretreatment | Estriol Treatment | Post treatment | Estriol Treatment |
|---|---|---|---|
| I I I*⁺I I I* | I I I*I I I*⁺ | I I I*I I I* | I I I I* |
| months 1-6 | months 7-12 | months 13-18 | months 19-22 |

ESTRIOL THERAPY FOR MULTIPLE SCLEROSIS AND OTHER AUTOIMMUNE DISEASES

This present application is a Continuation Application of U.S. patent application Ser. No. 10/131,834 filed Apr. 24, 2002, now U.S. Pat. No. 6,936,599 which claims the benefit of U.S. Provisional Application No. 60/286,842, filed Apr. 25, 2001.

This invention was made with Government support under Grant No. NS 36680 awarded by the National Institute of Health and the National M.S. Society under Grant Nos. JF 2094 and RG 3016. The government has certain rights in this invention.

BACKGROUND OF THE INVENTION

1. Field of the Invention

This invention relates generally to steroidal therapies for treating autoimmune diseases and, more particularly, to administering primary agents being estrogens or estrogen receptor active agents for the treatment of cell mediated diseases. Optionally, secondary agents which effect the immune system may also be co-administered. Finally, treatment kits are provided containing at least one primary agent and at least one secondary agent for treating a patient presenting with symptomology of an autoimmune disease.

2. General Background and State of the Art

There is a distinct female preponderance of autoimmune diseases during the reproductive ages including multiple sclerosis (MS), rheumatoid arthritis (RA), uveitis, myesthenia gravis (MG), Sjogren's syndrome, and Hashimoto's thyroiditis.

For example, MS is a chronic, and often debilitating disease affecting the central nervous system (brain and spinal cord). MS affects more than 1 million people worldwide and is the most common neurological disease among young adults, particularly woman. The exact cause of MS is still unknown. MS attacks the nervous system resulting in myelin sheaths surrounding neuronal axons to be destroyed. This demyelinization can cause weakness, impaired vision, loss of balance, and poor muscle coordination. MS can have different patterns, sometimes leaving patients relatively well after episodes of acute worsening, sometimes leading to progressive disability that persists after episodes of worsening. In the worst cases the disease can lead to paralysis or blindness.

Steroid hormones or sex-linked gene inheritance may be responsible for the enhanced susceptibility of women to these autoimmune diseases. A role for steroid hormones in susceptibility to autoimmune disease is supported by observations of alternations in disease symptomology, with alterations in sex hormone levels such as during pregnancy, menopause or exogenous hormone administration (in the form of hormone replacement (HRT) or oral contraceptives (ORC)). For example, women with MS and RA have been reported to experience remission of symptoms during late gestation. Particularly, MS patients have been reported to show a decrease in relapse rate in pregnancy.

Normally, cell-mediated immunity is mediated by T helper cell (Th1) secretion of interferon gamma (IFN-γ) and tumor necrosis factor beta (TNF-γ). In contrast, humoral immunity is mediated by another group of T helper cells (Th2) secreting interleukin (IL)-10, IL-4, IL-5 and IL-6. A systemic shift toward humoral immunity (or Th2-mediated immunity) has been noted during pregnancy. During pregnancy, cell-mediated immunity is decreased and humoral-mediated immunity is increased thereby promoting fetal survival. Thus, this systemic shift in the immune system may explain why cell-mediated diseases, including MS and RA have been reported to improve during pregnancy.

Although a shift toward humoral-mediated immunity has been demonstrated during human pregnancy, mechanisms which induce this shift remain unclear. One possibility is local production of Th2 (or humoral mediated) cytokines by the placenta. Another possibility is the production of Th2 cytokines by immune cells, consequent to changed levels of steroid hormones during pregnancy. Consistent with the latter possibility, in vitro studies have demonstrated the ability of the steroid progesterone to increase IL-4 production and the ability of the steroid 17β-estradiol to increase IL-10 production during T-lymphocyte responses. However, it remains unclear what cellular mechanisms are involved in regulating in vivo amelioration of autoimmune symptomology.

Examples of potential candidates which effect may effect MS during pregnancy include: Sex hormones (estrogens, progesterone), cortisol, vitamin D, alpha-fetoprotein, human chorionic gonadotropin and pregnancy specific glycoproteins.

Further, some studies have suggested that a unique pregnancy factor termed "early pregnancy factor" is responsible for improved progression of cell-mediated autoimmune diseases during pregnancy. Other studies have suggested a role for microchimerism. Still others suggest a role for local factors such as TGFβ or estriol (E3) which is known to be produced by the placenta during pregnancy. Of note, E3 is at its highest serum levels in the third trimester of pregnancy. However, E3's role in ameliorating symptoms of autoimmune diseases in humans is unclear.

Studies in laboratory animals have established that experimental autoimmune encephalomyelitis (EAE) and other Th1 (cell-mediated) autoimmune diseases in mice improve during pregnancy.

Specifically, treatment with late-pregnancy levels of estriol or supraphysiological doses of estradiol (5 times pregnancy levels) were shown to delay the onset of clinical EAE after disease was experimentally induced by immunization of mice (Jansson et al. 1994). However, there was no investigation as to how estrogens delayed the day of onset of disease, nor as to whether disease severity was effected in these animals once symptomology occurred.

In another study, it was shown that EAE disease severity could be reduced by treatment with estriol, either before or after disease onset. Treatment of EAE mice with 90 day release pellets of 5 milligrams or 15 milligrams of estriol (E3) was shown not only to decrease disease severity but also to enhance autoantigen specific humoral-immunity, increase production of the Th2 cytokine IL-10 and reduced inflammation and demyelination in EAE mice. Importantly, these changes in the disease were induced by a dose (5 mg) which was shown to yield estriol levels in serum that were similar to those which occur during late pregnancy (Kim et al., *Neurology*, 50(4 Supp. 4):A242-245, April 1998, FASEB *Journal* 12(4):A616, March 1998 and *Neurology* 52(6):1230-1238, April 1999; herein incorporated by reference). Thus, these results suggested that steroid hormones, and estriol in particular, may be involved in the amelioration of autoimmune reactions in the EAE animal model.

Other groups later demonstrated that estrogen potentiated the effects of treatment with TCR proteins to reduce autoimmune reactions in EAE mice. Offner, et al. *FASEB Journal* 14(6):A1246, April 2000; *Int. Journal of Mol. Medicine* 6 (Supp. 1): S8, October 2000 and *Journal of Clin. Invest.* 105(10):1465-1472, May 2000). Further, it was shown in animal studies that estrogen suppressed the onset EAE in mice (Ito, et al. *Journal of Immunology,* 167(1): 452-52, 2001) and that presumed diestrus levels of estrogens reduced some manifestations of active EAE in mice. Bebo et al. *Journal of Immunology* 166(3): 2080-9, 2001.

However, the etiology and disease progression of EAE and MS are not identical, thus it is unclear that estrogens alone would be effective in ameliorating autoimmune responses in human patients. Indeed, not only is it unknown whether pregnancy doses of estrogens might be protective in humans with autoimmune disease, it is unclear even in mice whether low doses of estrogens are protective. For example, it has been reported by some that ovariectomy of female mice makes EAE disease worse (Matejuk et al., 2001), while others have found that ovariectomy had no effect on disease severity (Kim et al., 2001; Voskuhl and Palaszynski, 2001a; Voskuhl and Palaszynski, 2001b). Thus, it is controversial whether low levels of estrogens, as they exist during the menstrual cycle, are protective even in mice.

Data from human studies to date have shown no clear benefit of steroids in treating any autoimmune disease. In humans, administration of available hormone therapies (including HRTs and OCPs) containing a mixture of sex hormones cause some autoimmune diseases to improve while others worsen.

For example, there has been no conclusive evidence that women are protected from or have a decrease in symptomology or relapse rates due to sex steroids. One study noted that past use of oral contraceptives in healthy women had no effect on subsequent risk to develop MS (Hernan et al. 2000). Further, another study found that the incidence rates for MS in current users were not decreased as compared to never-users (Thorogood and Hannaford, 1998). Thus, low dose of the estrogens in oral contraceptives are not of sufficient type or dose to ameliorate the immunopathogenesis of MS even temporarily during intercurrent use. At best, in one study, patients had the subjective impression that pre-existing MS symptoms (as opposed to relapse rates) worsen during the premenstrual period and that the use of oral contraceptives may have decreased this worsening (Zorgdrager and De Keyser, 1997). Importantly, the lack of reports of an effect of oral contraceptive therapy on MS relapses is in marked contrast to what has been observed during pregnancy.

In contrast, it has been shown that women had a lower the risk of developing MS during pregnancy compared to non-pregnant states (Runmarker and Andersen, 1995). Due to the numerous changes that occur during pregnancy, hormonal and nonhormonal (as listed above), the etiology of the beneficial effect of pregnancy may or may not be related to sex steroid fluctuations. It has also been reported for decades that pregnancy decreases MS relapses (Abramsky, 1994; Birk et al. 1990; Birk et al, 1998; Damek and Shuster, 1997; Runmarker and Andersen, 1995; Confavreux et al., 1998). These studies have shown that the latter part of pregnancy is associated with a significant reduction in relapses, while there is a rebound increase in relapses post partum. In contrast, the absence of such an effect on relapses during OCP or HRT indicate that low level sex steroids are not adequate to treat these symptoms.

Further, women having rheumatoid arthritis that were treated with HRT did not show significant improvement in their symptomology. DaSilva and Hall, *Baillieres Clinical Rheumatology* 1992, 6:196-219; Bijisma at al. *Journal of Repro. Imm.* 28(3-4):231-4, 1992; Hall et al. *Annals of the Rheumatic Diseases,* 53(2): 112-6, 1994.

Thus, the low doses of hormones found naturally during the menstrual cycle or in ORT and HRT have not been shown to be effective at ameliorating the symptomology of autoimmune diseases. This is in spite of the observation that women having MS have a decreased relapse rate during late pregnancy. Thus, a challenge has been to identify a hormone and a treatment dose that is therapeutic in treating particular autoimmune diseases, while minimizing undesirable side effects. Obviously, the dose and method of administration of steroids in humans differs from steroid treatment in laboratory animals due to toxic effects of prolonged exposure by patients to steroid hormones. In particular, there are clinical concerns of inducing breast or endometrial cancers in women requiring long term exposure to steroid hormones.

INVENTION SUMMARY

A general object of the present invention is to provide a method of administering steroid hormones to mammals to treat autoimmune related diseases, more particularly, Th1-mediated (cell-mediated) autoimmune diseases including: multiple sclerosis (MS), rheumatoid arthritis (RA), autoimmune thyroiditis, uveitis and other autoimmune diseases in which clinical symptomology has shown improvement during the third term of pregnancy.

In accordance with one aspect of the present invention, these objectives are accomplished by providing a treatment for autoimmune related diseases with a selected dose and course of a primary agent being an estrogen or estrogen receptor-effective composition.

In accordance with one aspect of the present invention, these objectives are accomplished by providing a patient with a therapeutically effective amount of estriol, comprising from about 4 to 16 milligrams per day, or more specifically, about 8 milligrams once daily via oral administration.

In accordance with another aspect of the present invention, these objectives are accomplished by providing a therapeutically effective amount of a primary agent in combination with a therapeutically effective amount of a secondary active agent, such as progesterone, glucocorticoids and/or known or experimental drugs used to treat autoimmune diseases.

The above described and many other features and attendant advantages of the present invention will become apparent from a consideration of the following detailed description when considered in conjunction with the accompanying drawings.

DETAILED DESCRIPTION OF THE PREFERRED EMBODIMENTS

Figures 1A, 1B:
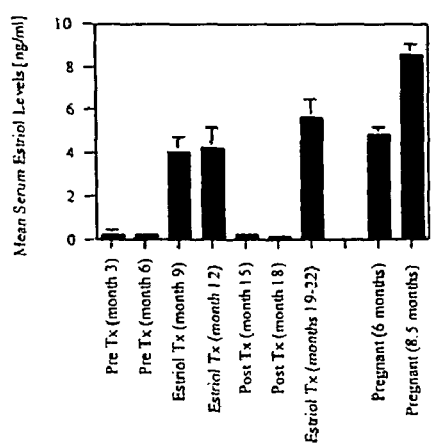
FIG. 1*a* is a schematic depicting the trial design described in Example 1.
FIG. 1*b* is a bar graph depicting human serum levels during pregnancy, estriol treatment (Tx), and pretreatment (Pre Tx levels).

This description is not to be taken in a limiting sense, but is made merely for the purpose of illustrating the general principles of the invention. The section titles and overall organization of the present detailed description are for the purpose of convenience only and are not intended to limit the present invention.

Generally, the invention involves a method of treating mammal exhibiting clinical symptoms of an autoimmune disease comprising administering a primary agent at a therapeutically effective dosage in an effective dosage form at a selected interval. The treatment is aimed at reducing the symptomology and/or progression of the disease. In the preferred embodiment of the invention, human patients clinically diagnosed with MS (including both relapsing remitting or secondary progressive type patients) are treated with an oral preparation of 8 milligrams estriol daily and have ameliorated symptomology.

Amelioration of the autoimmune disease refers to any observable beneficial effect of the treatment. The beneficial effect can be evidenced by a delayed onset or progression of disease symptomology, a reduction in the severity of some or all of the clinical symptoms, or an improvement in the overall health.

For example, patients who have clinical symptoms of an autoimmune disease often suffer from some or all of the following symptoms: worsening of pre-existing symptoms (such as joint pain in rheumatoid arthritis), the appearance of new symptoms (new joints affected in rheumatoid arthritis) or increased generalized weakness and fatigue. MS patients in particular suffer from the following symptoms: weakness, numbness, tingling, loss of vision, memory difficulty and extreme fatigue. Thus an amelioration of disease in MS would include a reduction in the frequency or severity of onset of weakness, numbness, tingling, loss of vision, memory difficulty and extreme fatigue. On imaging of the brain (MRI) amelioration of disease would be evidenced by a decrease in the number or volume of gadolinium enhancing lesions, a stabilization or slowing of the accumulation of T2 lesions and/or a slowing in the rate of atrophy formation. Immunologically, an increase in Th2 cytokines (such as IL-10) and a decrease in Th1 cytokines (such as interferon gamma) would be associated with disease amelioration.

Patients may also express criteria indicating they are at risk for developing autoimmune diseases. These patients may be preventatively treated to delay the onset of clinical symptomology. More specifically, patients who present initially with clinically isolated syndromes (CIS) may be treated using the treatment paradigm outlined in this invention. These patients have had at least one clinical event consistent with MS, but have not met full criteria for MS diagnosis since the definite diagnosis requires more than one clinical event at another time (McDonald et al., 2001). Treatment of the present invention would be advantageous at least in preventing or delaying the development of clinically definite MS.

PRIMARY AGENT. The primary agent useful in this invention is a steroid hormone, more particularly a estrogen or a steroidal or non-steroidal estrogen receptor active agent. Most preferably the primary agent is estriol (estra-1,3,5(10)-triene-3,16,17-triol, E3, such as estriol succinate, estriol dihexanate or estriol sulfmate. However, the primary agent may be precursors or analogs of estriol (such as nyestriol), estrone (E1) or precursors or analogs of estrone, 17β-estradiol (E2) or precursors (including aromatizable testosterone) or analogs of 17β-estradiol.

The primary agent may also be a metabolite or derivatives of E1, E2 or E3 which are active at the estrogen receptor α or β. Metabolites and derivatives may have a similar core structure to E1, E2 or E3 but may have one or more different groups (ex. hydroxyl, ketone, halide, etc.) at one or more ring positions. Synthetic steroids which are effective at estrogen receptor are also useful in this invention, such as those described in WO 97/08188 or U.S. Pat. No. 6,043,236 to Brattsand.

The primary agent may also be an estrogen receptor α or β agonists and/or antagonist. These agonists or antagonists may be steroidal or non-steroidal agents which bind to and/or cause a change in activity or binding of at least one of the estrogen receptor α or β subtypes. For example, specific agonists of ER alpha and ER beta may be useful in this invention (Fritzmeier, et al.). Doses of these agonists may be titrated to achieve an effect on disease similar to that which is observed during pregnancy and during treatment with pregnancy doses of estriol by methodologies known to those skilled in the art of steroid pharmacology.

Any one or combination of these estrogens or estrogen receptor active agents may be used to treat the selected autoimmune disease. The selection of the estrogens or estrogen receptor active agents can be made considering secondary side effects of the treatment to the patient. For example, estriol may be selected over 17β-estradiol, because estriol causes minimal endometrial proliferation and is not associated with increased risk of breast cancer. Minimal endometrial proliferation is observed when the long-acting estriol derivative, nyestriol is used. Indeed, because estriol has partial antagonist action on the binding of 17β-estradiol to the estrogen receptor in vivo, estriol was at one point in the past considered as a therapeutic agent for treatment and prevention of breast cancer.

THERAPEUTICALLY EFFECTIVE DOSAGE OF THE PRIMARY AGENT. A therapeutically effective dose of the primary agent is one sufficient to raise the serum concentration above basal levels, and preferably to pregnancy levels or above pregnancy levels. Most preferably, the therapeutically effective dosage of the primary agent is selected to result in serum levels in a patient equivalent to the steroid hormone level of that agent in women in the second or third trimester of pregnancy.

For example, during the normal female menstrual cycle estradiol levels are in the range of about 350 pg/ml serum. During pregnancy, there is about a 100 fold increase in the level of estradiol to about 10,000 to about 35,000 pg/ml serum. Correale, et al. *Journal of Immunology* 161:3365 (1998) and Gilmore, et al. *Journal of Immunology* 158:446. In contrast, estriol levels are undetectable during the menstrual cycle in the non-pregnant state. Estradiol levels rise progressively during pregnancy to levels from 3,000 to 30,000 pg/ml (3 to 30 ng/ml) (wwwv.il-st-acad-sci.org/steroid1.html#se3t).

In one embodiment, where the primary agent is estriol, the preferable dose is from about 4 to 16 milligrams daily, and more specifically, about 8 milligrams daily. In this embodiment, blood serum levels preferably reach at least about 2 ng/ml, may reach about 10 to about 35 ng/ml, or most preferably about 20-30 ng/ml. Sicotte et al. *Neurology* 56:A75. In some embodiments, estradiol (E2) levels would preferably reach at least about 2 ng/ml and most preferably about to 10-35 ng/ml. In some embodiments, estrone (E1) levels would preferably reach at least about 2 ng/ml and most preferably about 5-18 ng/ml (DeGroot and Jameson, 1994).

The dosage of the primary agent may be selected for an individual patient depending upon the route of administration, severity of disease, age and weight of the patient, other medications the patient is taking and other factors normally considered by the attending physician, when determining the individual regimen and dosage level as the most appropriate for a particular patient.

The use of this group of primary agents is advantageous in at least that other known or experimental treatments for cellular mediated autoimmune diseases are chemotherapeutic immunosuppresants which have significant risks and side effects to patients, including decreasing the ability of the patient to fight infections, inducing liver or heart toxicity which are not caused by estrogen treatment. Other agents used in MS do not cause these side effect, but are associated with flu-like symptoms or chest tightness. Further, these previously used agents are associated with local skin reactions since they entail injections at frequencies ranging from daily to once per week.

DOSAGE FORM. The therapeutically effective dose of the primary agent included in the dosage form is selected at least by considering the type of primary agent selected and the mode of administration. The dosage form may include the active primary agent in combination with other inert ingredients, including adjutants and pharmaceutically acceptable carriers for the facilitation of dosage to the patient as known to those skilled in the pharmaceutical arts. The dosage form may be any form suitable to cause the primary agent to enter into the tissues of the patient.

In one embodiment, the dosage form of the primary agent is an oral preparation (liquid, tablet, capsule, caplet or the like) which when consumed results in elevated serum estrogen levels. The oral preparation may comprise conventional carriers including diluents, binders, time release agents, lubricants and disinigrants.

In other embodiments of the invention, the dosage form may be provided in a topical preparation (lotion, creme ointment or the like) for transdermal application. Alternatively, the dosage form may be provided in a suppository or the like for transvaginal or transrectal application.

That estrogens or estrogen receptor active agents can be delivered via these dosage forms is advantageous in that currently available therapies, for MS for example, are all injectables which are inconvenient for the user and lead to decreased patient compliance with the treatment. Non-injectable dosage forms are further advantageous over current injectable treatments which often cause side effects in patients including flu-like symptoms (particularly, β interferon) and injection site reactions which may lead to lipotrophy (particularly, glatiramer acetate copolymer-1).

However, in additional embodiments, the dosage form may also allow for preparations to be applied subcutaneously, intravenously, intramuscularly or via the respiratory system.

SECONDARY ACTIVE AGENTS. Any one or a combination of secondary active agents may be included in the dosage form with the primary agent. Alternatively, any one or a combination of secondary active agents may be administered independently of the primary agent, but concurrent in time such that the patient is exposed to at least two agents for the treatment of their immunological disease.

The secondary agents are preferably immunotherapeutic agents, which act synergistically with the primary agent to diminish the symptomology of the autoimmune disease. Secondary active agents may be selected to enhance the effect of the estrogen or estrogen receptor active agent, reduce the effect of the estrogen or estrogen receptor active agent or effect a different system than that effected by the estrogen or estrogen receptor active agent.

Secondary active agents include immunotherapeutic agents which cause a change in the activity or function of the immune system.

In one embodiment, a secondary agent may be a therapeutically effective amount of progesterone, precursor, analog or progesterone receptor agonist or antagonist. Most preferably, the secondary agent is 100-200 milligrams of progesterone administered daily. Progesterone in combination with estrogen or estrogen receptor active agent treatment is advantageous in at least protecting patients against risks associated with long term estrogen exposure, including, but not limited to endometrial proliferation and breast cancers.

In another embodiment, a secondary agent may be a therapeutically effective amount of glucocorticoid, precursor, analog or glucocorticoid receptor agonist or antagonist. For example, prednisone may be administered, most preferably in the dosage range of about 5-60 milligrams per day. Also, methyl prednisone (Solumedrol) may be administered, most preferably in the dosage range of about 1-2 milligrams per day. Glucocorticoids are currently used to treat relapse episodes in MS patients, and symptomatic RA within this dosage range.

In other embodiments, a secondary agent may be selected from the group immunotherapeutic compounds. For example, as β-interferon (Avonex® (interferon-beta 1a), Rebiff® (by Serono); Biogen, Betaseron® (interferon-beta 1b) Berlex, Schering), glatiramer acetate copolymer-1 (Copaxone®; Teva), antineoplastics (such as mitoxantrone; Novatrone® Lederle Labs), human monoclonal antibodies (such as natalizumab; Antegren® Elan Corp. and Biogen Inc.), immunosuppressants (such as mycophenolate mofetil; CellCept® Hoffman-LaRoche Inc.), paclitaxel (Taxol®; Bristol-Meyers Oncology), cyclosporine (such as cyclosporin A), corticosteroids (glucocorticoids, such as prednisone and methyl prednisone), azathioprine, cyclophosphamide, methotrexate, cladribine, 4-aminopyridine and tizanidine.

By way of example, which is consistent with the current therapeutic uses for these treatments, Avonex® in a dosage of about 0 to about 30 mcg may be injected intramuscularly once a week. Betaseron® in a dosage of about 0 to about 0.25 mg may be injected subcutaneously every other day. Copaxone® in a dosage of about 0 to about 20 mg may be injected subcutaneously every day. Finally, Rebiff® may be injected at a therapeutic dose and at an interval to be determined based on clinical trial data. However, dosages and method of administration may be altered to maximize the effect of these therapies in conjunction with estrogen treatment. Dosages may be altered using criteria that are known to those skilled in the art of diagnosing and treating autoimmune diseases.

Preferably, secondary agents would be administered in the dosage ranges currently used to treat patients having autoimmune diseases, including MS patients. Alternatively, the secondary agents may be administered at a reduced dose or with reduced frequency due to synergistic or duplicative physiological effects with the primary agent.

Preferably, patients exhibiting symptomology of autoimmune diseases are treated with the above agents (estrogen or estrogen receptor active agents with or without secondary agents). Most preferably, patients exhibit autoimmune diseases marked by improvement in symptomology at least during a treatment regimen, including but not limited to that reflecting patterns observed during the second or third trimester of pregnancy.

KITS. In another aspect of this invention kits are provided for use by the treating physician in the clinic or prescribed patient for self-administration of treatment. The kits of this invention include at least one primary agent and one secondary agent in the appropriate dosages and dosage form for the treatment of the patient's clinical symptoms.

In a first embodiment of the kit, the primary agent is estriol in doses of about 4-16 milligrams and the secondary agent is progesterone in doses of about 100 to about 200 milligrams.

In a second embodiment of this kit, the primary agent is estriol in doses of about 4-16 milligrams and the secondary agent is a glucocorticoid, such as prednisone (about 5-60 milligrams per day) or methyl prednisone (1-2 milligrams per day).

In a third embodiment of this invention, the primary agent is estriol in doses of about 4-16 milligrams and the secondary agent is β-interferon in doses of about 0.25 milligrams of Betaseron® or 30 mcg of Avonex®. In a fourth alternate embodiment of the kit, the primary agent is estriol in doses of about 4 to about 16 milligrams and the secondary agent is glatiramer acetate copolymer in doses of about 20 milligrams of Copaxone®.

The kit also preferably contains instructions for use of the kit by the use by the treating physician or patients to treat their autoimmune disease. Such information would include at least the schedule for the administration of the primary agent dose and the secondary agent dose.

Although the present invention has been described in terms of the preferred embodiment above, numerous modifications and/or additions to the above-described preferred embodiments would be readily apparent to one skilled in the art.

Example 1

Methods: Trial Design. A crossover design was used with monthly brain MRIs during the six month pretreatment period, the six month treatment period with oral estriol (8 milligrams/day) and the six month post treatment period, with clinical and laboratory evaluations as demonstrated (FIG. 1A).

Inclusion Criteria. Women with clinically definite MS, ages 18-50, with an EDSS 0-6.5 who had been off interferon beta and copolymer-1 for at least six months, and had no steroid treatment for at least three months were eligible. At least 5 cm$^3$ of lesion burden on a screening T2 weighted brain MRI was required. Subjects who were pregnant or nursing, on oral contraceptives or hormone replacement therapy, or who had a history of thrombosis, neoplasm or gynecologic disease, or who had been treated in the past with total lymphoid irradiation, monoclonal antibody, T cell vaccination, cladribine or bone marrow transplantation were excluded.

Patients. Twelve female patients with clinically definite MS were enrolled. Six had RR disease and six had SP disease. All six RR and four of six SP patients completed the entire 18 month study period. One SP patient was discontinued from the study because of prolonged treatment with steroids for tonic spasms by an outside neurologist and the other did not wish to go untreated in the post treatment period. Of the ten patients who completed the entire study, the mean age was 44 years (range 28 to 50 years) and the mean EDSS was 3.3 (range 1.0 to 6.5). The mean EDSS score for the SP patients was 5.0 while the mean EDSS for the RR patients was 2.2. The 18 month trial was extended in RR patients whereby treatment was re-instituted.

Medication. For the initial treatment phase, micronized, U.S.P. graded estriol powder (Medisca, Inc., Plattsburg, N.Y.) was put into capsules by UCLA Pharmaceutical Services. During the extension re-treatment phase in the RR patients, all but one received a capsule of estriol (8 milligrams/day) plus progesterone (100 milligrams/day), while the single RR patient who had a hysterectomy received only estriol (8 milligrams/day) (Women's International Pharmacy, Madison, Wis.).

Clinical and Safety Measures. Subjects were evaluated using the Kurtzke's Expanded Disability Status Scale (EDSS) by the same neurologist (RV) throughout the study. At each visit the study nurse (RK) administered the paced auditory serial addition test (PASAT) and the 9-hole peg test. Blood was drawn for SMAL2, cholesterol panel, blood counts and hormone levels (estriol, estradiol, estrone, LH, FSH, cortisol, progesterone). Estriol levels in serum were determined by ELISA according to manufacturer's instructions (Oxford Biomedical, Oxford, Mich.).

Delayed Type Hypersensitivity Responses (DTH). DTH to tetanus (Tetanus Toxoid, Wyeth Laboratories, Marietta, Pa.) and candida (Candin, Allermed Laboratories, San Diego, Calif.) were tested at two timepoints, once in the pretreatment period at study month 3 and once at the end of the treatment period at study month 12 (FIG. 1a). A group of six untreated healthy control women were also tested twice, spanning the same time interval (9 months). 0.1 ml of each solution was injected intradermally on the anterior surface of the forearm. Induration at each injection site was read after 48 hours. Each site was measured twice, once vertically and once horizontally with the average recorded. The same nurse (RK) administered all injections and read all responses on all subjects at both time points.

Reverse Transcription and Polymerase Chain Reaction. Peripheral blood mononuclear cells (PBMCs) were isolated from heparinized venous blood and cryopreserved. PBMCs were thawed in parallel from a given patient during the two pre-treatment timepoints and the two treatment timepoints. Total RNA was isolated, DNA was removed and mRNA was reverse transcribed. Both IFN-γ and actin were amplified from the same cDNA, however, the cDNA was diluted 1:9 prior to amplification for actin. Amplification was done in 1 mM Milligrams $Cl_2$ using IFNγ and actin primer sequences (Life Technologies, Rockville, Md.). Complementary DNA was amplified for 35 cycles: 45"@95° C., 60"@54° C. and 45"@72° C. PCR products were separated on a 1.5% agarose gel containing ethidium bromide and densitometry performed.

MRIs. Scans were performed on a 1.5T G.E. scanner. The pulse sequences obtained were a T1-weighted scan with and without gadolinium (Omniscan 0.1 mmol/kg) and a PD/T2 weighted scan. Digitized image data was transferred to a SGI workstation (Silicon Graphics, Inc) for further processing. The number and volume of new and total gadolinium enhancing lesions was determined using a semiautomated threshold based technique (Display, Montreal Neurological Institute) by a single experienced operator (NS). The operator was blinded as to whether patients had RR or SP disease. To calculate T2 volumes, a custom semiautomated, threshold based, seed-growing algorithm was used to determine lesion volume after skull stripping, rf correction and spatial normalization. All scans were counted by the same technician who was blinded as to whether patients had RR or SP disease.

Statistical Analysis. One sample, paired, t tests were used to ascertain significance of percent changes in DTH responses, IFNγ levels and PASAT cognitive testing scores during treatment as compared to pretreatment. The nonparametric, Wilcoxon's signed rank test was used for statistical comparisons in enhancing lesion numbers and volumes on MRI between the six month baseline period and each treatment period, post treatment period and re-treatment period.

Results. Estriol levels and tolerability. Serum estriol levels during treatment and re-treatment approximated those observed in women who were six months pregnant, but were lower than those who were 8.5 months pregnant (FIG. 1B). Consistent with previous reports, estriol was well tolerated with only menstrual cycle abnormalities. There were no significant alterations in any laboratory measures including LH, FSH, cortisol, progesterone, estradiol and estrone.

Figure 2:
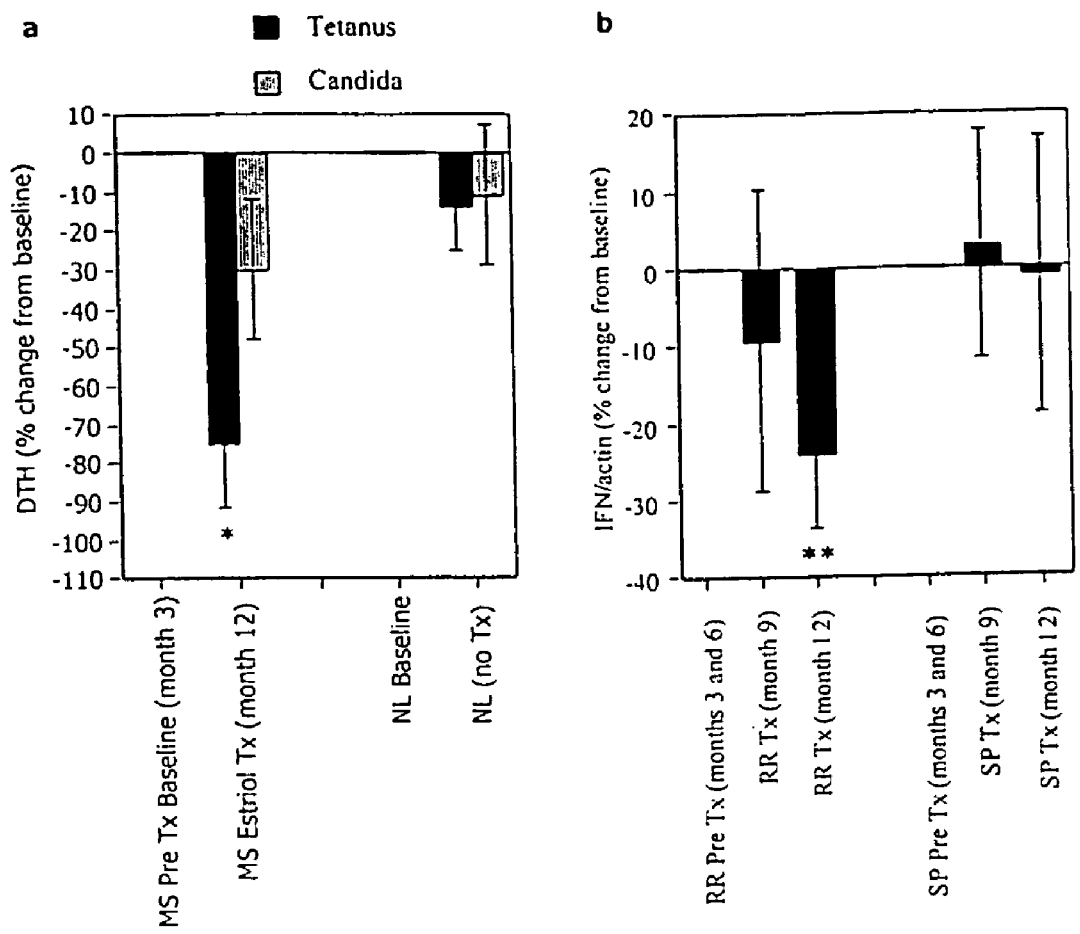
FIG. 2*a* is a bar graph describing the Delayed Type Hypersensitivity (DTH) responses to tetanus and to candida.
FIG. 2*b* is a bar graph depicting levels of IFNγ between treatment groups.

Immune Responses. Skin testing to tetanus and candida were performed once in the pretreatment period and once at the end of the treatment period to determine whether they might be decreased with treatment. DTH responses to tetanus were significantly, P=0.006, decreased at study month 12, when patients had been on estriol for six months, as compared to DTH responses at study month 3, the pretreatment baseline (FIG. 2A). DTH responses to candida were decreased less dramatically and more variably. The significant decrease in DTH responses to tetanus from pretreatment (month 3) to treatment (month 12) was not merely due to repeat testing at nine months since healthy, untreated female controls tested at baseline, then again after nine months, did not demonstrate a significant decrease in DTH responses as compared to their baseline. These findings are consistent with an estriol induced down-regulation of Th1 responses in vivo during treatment.

IFNγ is a signature cytokine for Th1 responses. Therefore, we assessed IFNγ levels by RT-PCR of unstimulated peripheral blood mononuclear cells (PBMCs) derived ex vivo from patients during the pretreatment and the treatment periods. In the six RR patients, levels of IFNγ were variably decreased at study month 9 (after three months of estriol treatment) and then significantly decreased, P=0.003, at study month 12 (after six months of estriol treatment) as compared to baseline pretreatment levels (months 3 and 6) (FIG. 2B). In contrast, there was no decrease in IFNγ in the four SP patients. These data are consistent with the concept that the immune system of RR patients, as compared to SP patients, may be more amenable to treatments that aim to decrease Th1 responses. Also, the observation that estriol treatment can alter cytokine production by PMBCs is consistent with reports demonstrating estrogen receptors α and β in immune tissues and cells.

Figure 3:
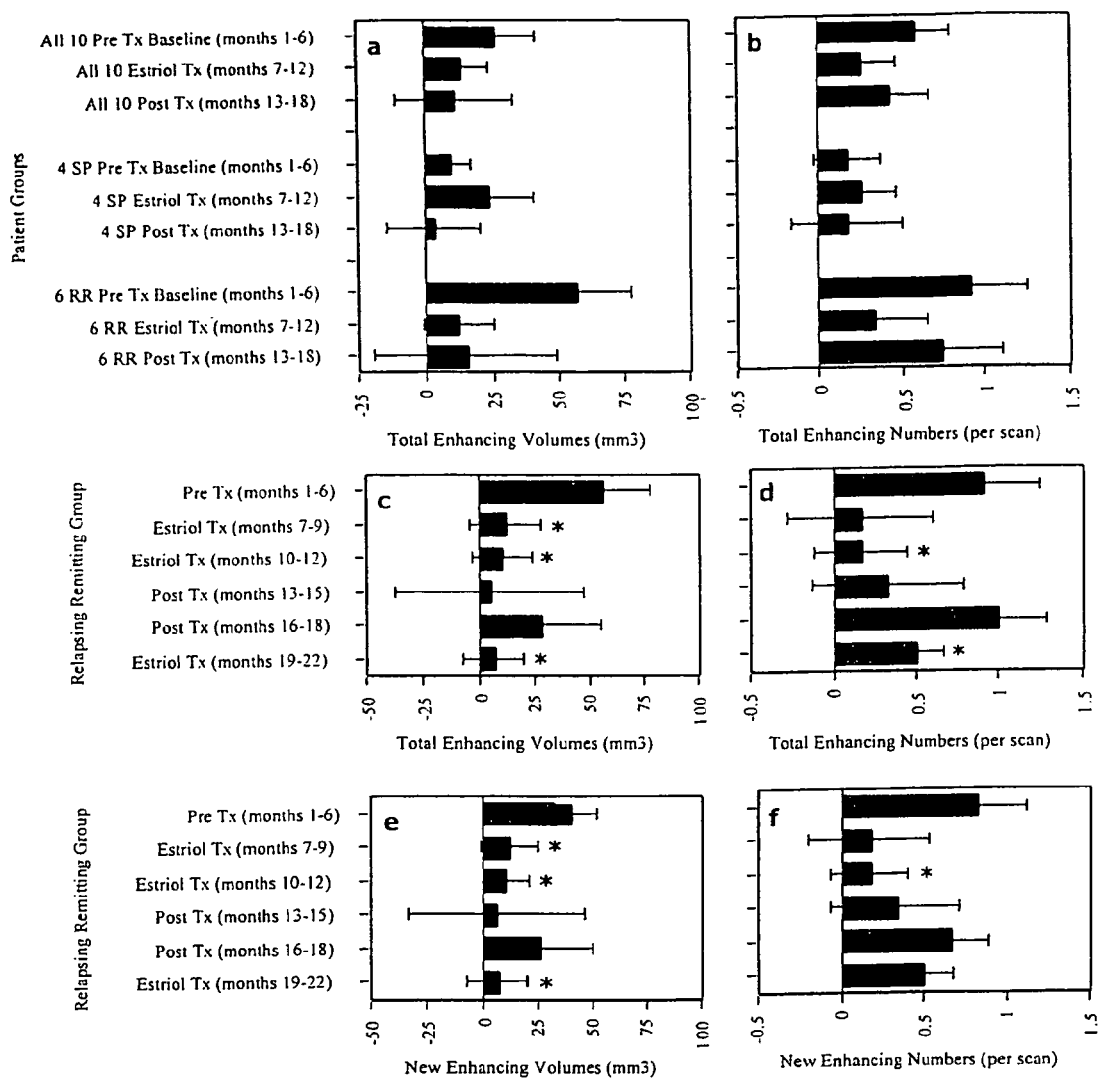
FIG. 3*a-f* are bar graphs depicting each patient's gadolinium enhancing lesion volumes on serial cerebral MRIs which were assessed at each month during the pretreatment, estriol treatment and post treatment periods.

MRIs. Based on the protective effect of pregnancy on relapse rates in MS patients and the association of gadolinium enhancing lesions with relapses, we hypothesized that estriol treatment would have an anti-inflammatory effect as manifested by decreases in enhancing lesions on serial brain MRIs. Compared to the six month pretreatment baseline period, the total volume and number of enhancing lesions for all ten MS patients (6RR, 4SP) decreased during the treatment period. This improvement in the group as a whole was driven by the beneficial effect of estriol treatment in the RR, not the SP, group (FIGS. 3A and 3B). Therapeutic effects of estriol treatment in the RR group were therefore examined in further detail. Within the first three months of treatment of RR patients, median total enhancing lesion volumes were decreased by 79%, P=0.02, and numbers were decreased by 82%, P=0.09 (FIGS. 3C and 3D). They remained decreased during the next three months of treatment, with lesion volumes decreased by 82%, P=0.01, and numbers decreased by 82%, P=0.02. In the post treatment period, median total enhancing lesion volumes and numbers became variable in the first three months off treatment, before returning to near baseline levels in the last three months of the post treatment period. During the four month re-treatment extension phase, enhancing lesion volumes decreased again by 88%, P=0.008, and numbers decreased again, this time by 48%, P=0.04, as compared to original baseline (FIGS. 3C and 3D). Changes in median new enhancing lesion volumes and numbers followed similar patterns as median total lesion numbers and volumes (FIGS. 3E and 3F).

Median T2 lesion volumes for the whole group were 15.3 cm$^3$ (range 6.1-33.8), with no significant differences in median T2 volumes between RR and SP groups. Consistent with enhancing lesion data, serial T2 lesion volumes revealed that estriol treatment tended to be most beneficial in RR patients. In the RR group, median T2 lesion volumes remained stable during the six month treatment period (0% change), increased during the six month post treatment period (7.4% higher), and then declined in the four month re-treatment extension period (2.0% lower).

Clinical measures. Relapses were few and showed no significant changes during the study. In the six RR patients, one relapse occurred during the pretreatment period, one in the treatment period, two in the post treatment period and none in the re-treatment period. No relapses occurred in SP patients. EDSS and 9 Hole Peg Test scores showed no significant changes during the study (Table 1).

TABLE I

| Clinical Measures | | | | | | |
|---|---|---|---|---|---|---|
| | Pretreatment | | Estriol Treatment | | Post Treatment | |
| | 3 mo. | 6 mo. | 9 mo. | 12 mo. | 15 mo. | 18 mo. |
| EDSS scores | | | | | | |
| 6 RR | 2.2 | 2.0 | 1.5 | 1.7 | 1.8 | 1.8 |
| | (0.6) | (0.5) | (0.7) | (0.6) | (0.6) | (0.5) |
| 4 SP | 5.0 | 5.0 | 4.9 | 5.0 | 5.1 | 5.0 |
| | (0.9) | (0.9) | (1.0) | (0.9) | (1.1) | (0.8) |
| 9 Hole Peg Test scores | | | | | | |
| 6 RR | | | | | | |
| R | 22.2 | 21.8 | 22.5 | 21.5 | 21.0 | 21.4 |
| | (2.4) | (1.6) | (2.3) | (1.9) | (1.7) | (2.4) |
| L | 24.8 | 22.9 | 24.3 | 23.3 | 23.0 | 22.7 |
| | (3.2) | (1.6) | (2.5) | (2.1) | (2.1) | (2.3) |
| 4 SP | | | | | | |
| R | 26.8 | 29.9 | 30.2 | 31.7 | 29.4 | 34.0 |
| | (0.4) | (2.4) | (1.4) | (4.8) | (5.2) | (8.7) |
| L | 23.5 | 25.6 | 22.7 | 24.8 | 26.7 | 25.0 |
| | (1.4) | (2.5) | (1.7) | (2.6) | (0.7) | (1.8) |

Figure 4:
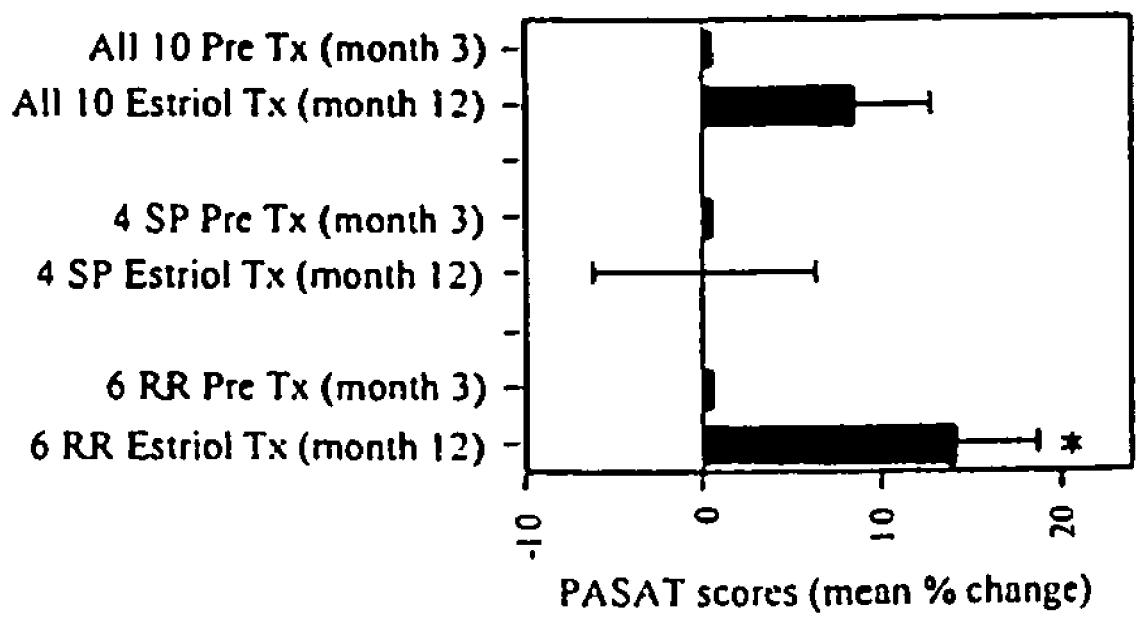
FIG. 4 is a bar graph depicting mean percent change in PASAT scores during treatment with estriol as compared to pretreatment.

Interestingly, PASAT cognitive testing scores were significantly improved in the RR group, but not in the SP group (FIG. 4). This improvement in PASAT scores in RR patients by 14.0% during treatment as compared to baseline, reached statistical significance, P=0.04. It is unlikely that this improvement was entirely due to a practice effect of repeated testing because of the long time interval between testing (9 months) and because alternate versions of the test were used in each patient. This beneficial effect of estriol treatment on PASAT scores of RR MS patients is consistent with previous reports describing a beneficial effect of estrogen replacement therapy in surgically menopausal women and high dose estrogen treatment in Alzheimer's disease. Sicottte, et al. *Treatment of Women with Multiple Sclerosis Using Pregnancy Hormone Estradiol: A Pilot Study. Neurology*, 56 (8 Supp. 3):A75, April 2001, and Sicotte, et al. *Treatment of Multiple Sclerosis with the Pregnancy Hormone Estradiol, Submitted to Neurology* 2002, are herein incorporated by reference in their entirety.

Example 2

Progesterone in combination with estrogen treatments has been shown to protect against endometrial proliferation and cancer. Indeed, estrogen cannot be given for a lengthy period of time in an "unopposed" fashion in any woman with a uterus. Thus, seven of the 12 patients wanted to remain on estriol after completion of the 18 month study. These patients were then put back on 8 milligrams of estriol and 100 milligrams of progesterone per day. In an extension phase of the study which began after completion of the post treatment phase. This extension phase was 4 months in duration. Each of the seven patients had an MRI every month during the 4 month extension phase. Additionally, each of the seven patients was examined neurologically and had serologic studies done at the end of this phase. No known negative effects 100 milligrams of progesterone in combination therapy with 8 milligrams of estriol treatment were noted.

In closing, it is noted that specific illustrative embodiments of the invention have been disclosed hereinabove. However, it is to be understood that the invention is not limited to these specific embodiments.

Accordingly, the invention is not limited to the precise embodiments described in detail hereinabove. With respect to the claims, it is applicant's intention that the claims not be interpreted in accordance with the sixth paragraph of 35 U.S.C. §112 unless the term "means" is used followed by a functional statement.

While the specification describes particular embodiments of the present invention, those of ordinary skill can devise variations of the present invention without departing from the inventive concept.

I claim:

1. A method of treating a human patient exhibiting clinical symptoms of multiple sclerosis comprising administering a therapeutically effective dosage of estriol of about 8 milligrams daily and a therapeutically effective dosage of glatiramer acetate copolymer-1 of about 20 milligrams daily.

2. The method of claim 1 wherein the treatment results in patient serum concentrations of estriol of about 2 to about 30 nanograms per milliliter.

3. The method of claim 1 wherein the treatment results in serum levels of estriol in a range about equivalent to those of a women in the mid second trimester through the end of the third trimester of pregnancy.

4. A method of treating a patient exhibiting a clinically isolated syndrome as a precursor to multiple sclerosis, comprising administering 8 milligrams of estriol daily and about 20 milligrams of glatiramer acetate copolymer-1 daily to delay the onset of additional symptoms of multiple sclerosis, wherein the combination of estriol and glatiramer acetate copolymer-1 has a synergistic therapeutic effect.

5. The method of claim 1 or 4 wherein the multiple sclerosis is a relapsing remitting form or secondary progressive form of multiple sclerosis.

* * * * *